(12) United States Patent
Arn et al.

(10) Patent No.: US 8,567,405 B2
(45) Date of Patent: Oct. 29, 2013

(54) FIXATION DEVICE

(75) Inventors: Thomas Arn, Lidingö (SE); Per Carlsson, Täby (SE); Kristian Wiberg, Ävsjö (SE)

(73) Assignee: Elekta AB (Publ), Stockholm (SE)

( * ) Notice: Subject to any disclaimer, the term of this patent is extended or adjusted under 35 U.S.C. 154(b) by 324 days.

(21) Appl. No.: 12/988,885

(22) PCT Filed: Apr. 22, 2008

(86) PCT No.: PCT/EP2008/054859
§ 371 (c)(1),
(2), (4) Date: Nov. 3, 2010

(87) PCT Pub. No.: WO2009/129847
PCT Pub. Date: Oct. 29, 2009

(65) Prior Publication Data
US 2011/0036356 A1 Feb. 17, 2011

(51) Int. Cl.
*A61G 15/00* (2006.01)
(52) U.S. Cl.
USPC .................................................. 128/845
(58) Field of Classification Search
USPC .......... 128/845, 846, 857, 859; 602/5, 17, 18; 606/130
See application file for complete search history.

(56) References Cited

U.S. PATENT DOCUMENTS

| | | | |
|---|---|---|---|
| 4,780,898 A | 10/1988 | Sundqvist | |
| 5,009,594 A * | 4/1991 | West | 433/73 |
| 5,531,229 A * | 7/1996 | Dean et al. | 128/866 |
| 5,730,745 A * | 3/1998 | Schulte et al. | 606/130 |
| 6,143,003 A * | 11/2000 | Cosman | 606/130 |
| 6,565,577 B2 * | 5/2003 | Cosman | 606/130 |
| 6,931,096 B2 | 8/2005 | Carlsson et al. | |
| 2002/0016600 A1 * | 2/2002 | Cosman | 606/130 |
| 2006/0115783 A1 * | 6/2006 | McLaren | 433/29 |

FOREIGN PATENT DOCUMENTS

| | | | | |
|---|---|---|---|---|
| DE | 3540756 A1 | | 5/1987 | |
| DE | 3540756 A1 * | | 5/1987 | A61C 19/045 |
| DE | 19619761 A1 * | | 11/1996 | A61B 19/00 |
| DE | 19619761 A1 | | 11/1996 | |

* cited by examiner

*Primary Examiner* — Patricia Bianco
*Assistant Examiner* — Raymond E Harris
(74) *Attorney, Agent, or Firm* — Birch, Stewart, Kolasch & Birch, LLP (57) ABSTRACT

This invention relates to a fixation device and a method for immobilizing a head of a patient relative a treatment unit or medical device during treatment of the head. The fixation device is provided with an interface unit adapted to be fixated in relation to an adaptor unit for connection to the treatment unit, or to a frame for connection to the medical device. Furthermore, the fixation device is provided with a bite-block for being inserted into a mouth of a patient and a positioning arrangement movably connecting the bite-block to the interface unit. The positioning arrangement is adapted to be fixated by means of an adhesive for fixation of the bite-block such that the head of a patient can be immobilized relative said adaptor unit or frame.

15 Claims, 4 Drawing Sheets

FIXATION DEVICE

FIELD OF THE INVENTION

The present invention relates to the field of radiation therapy. In particular, the invention relates to a fixation device for immobilizing a head of a patient relative a treatment unit during treatment of the head.

BACKGROUND OF THE INVENTION

The development of surgical techniques have made great progress over the years. For instance, for patients requiring brain surgery, non-invasive surgery is now available which is afflicted with very little trauma to the patient.

Stereotactic radiation surgery is such a minimally invasive treatment modality that allows delivery of a large single dose of radiation to a specific intracranial target while sparing surrounding tissue. Unlike conventional fractionated radiation therapy, stereotactic radiation surgery does not rely on, or exploit, the higher radiation sensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radiation resistant lesions can be treated. Because destructive doses are used, however, any normal structure included in the target volume is subject to damage.

One such non-invasive radiation therapy technique is so called LINAC (Linear Accelerator) radio therapy or radiation therapy. In a LINAC radiation therapy system, a collimated x-ray beam of a very high energy level is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain.

Another system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is, for example, referred to and described in U.S. Pat. No. 4,780,898.

In the system, the head of a patient is immobilized in a stereotactic instrument which defines the location of the treatment volume in the head. Further, the patient is secured in a patient positioning unit which moves the entire patient so as to position the treatment volume in coincidence with the focus point of the radiation unit of the radiation therapy system.

Consequently, in radiation therapy systems, such as a LINAC system or a Leksell Gamma Knife® system, it is of a high importance that the positioning unit which moves the patient so as to position the treatment volume in coincidence with the focus point of the radiation unit of the system is accurate and reliable. That is, the positioning unit must be capable of position the treatment volume in coincidence with the focus point at a very high precision. This high precision must also be maintained over time.

Hence, in order to obtain as favorable clinical effect as possible during the therapy is it of an utmost importance that the radiation reaches and hits the target, i.e. the treatment volume, with a high precision and thereby spares the healthy tissue being adjacent to and/or surrounding the treatment volume. To achieve this, the patient must be immobilized during a therapy session and, moreover, the position of the head of the patient must be the same in a therapy session as in a reference position, i.e. the position during the session when the pictures to create the therapy plan were captured by means of, for example, Computerized Tomography Imaging (CT-imaging). In fractionated radiation therapy where the patient is docked in and out of the radiation therapy system at each therapy session, it must thus be secured that the patient is positioned in exact the same way as in the session when the pictures were captured to create the therapy plan.

One prior art method for enabling measurements of the head of a patient and for immobilizing or fixating the head of the patient during neurological diagnosis, therapy or surgery, in particular during radiation therapy relatively an interface unit, frame or an adapter adapted to be fixated to a radiation therapy unit is a stereotactic frame provided with pin support members in form of posts having fixation pins for invasive fixation to the skull of a patient. In use during therapy or diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a patient table. This kind of frame is obviously not suitable for so called fractionated therapy.

Thus, there is a need for a head fixation arrangement that enables an accurate repeatable fixation of a head of a patient relative a radiation therapy unit during neurological diagnosis, therapy or surgery, to secure that the patient, or more specifically the head of the patient, is positioned in exact alignment to a reference position or at a known position in relation to the reference position, and that this done every single therapy occasion of the fractionated therapy.

SUMMARY OF THE INVENTION

An object of the present invention is to provide means for an accurate repeatable fixation of a head of a patient relative a treatment unit of a head treatment system during a treatment of the head or a portion thereof, to secure that the head of the patient is positioned and repositioned in exact alignment to a reference position or at a known position in relation to the reference position every single therapy occasion of a repeatable treatment.

This and other objects are achieved by providing a fixation device having the features defined in the independent claim. Example embodiments are defined in the dependent claims.

According to a first aspect of the present invention, there is provided a fixation device for immobilizing a head of a patient relative a treatment unit or medical device during treatment of the head. Said fixation device comprises an interface unit adapted to be fixated in relation to an adaptor unit for connection to the treatment unit, or to a frame for connection to the medical device. Furthermore, said fixation device further comprises a bite-block for being inserted into a mouth of a patient, and a positioning arrangement movably connecting the bite-block to the interface unit, wherein the positioning arrangement is adapted to be fixated by means of an adhesive for fixation of the bite-block such that the head of a patient can be immobilized relative said adaptor unit or frame.

According to a second aspect of the present invention, there is provided a method for immobilizing a head of a patient relative a treatment unit during treatment of the head. Said method comprising the steps of: providing a interface unit adapted to be fixated in relation to an adaptor unit for connection to the treatment unit, or to a frame for connection to the medical device; providing a bite-block adapted to be inserted into a mouth of a patient; providing a positioning arrangement adapted to movably connect the bite-block to the interface unit; positioning the bite-block in a co-operating position with a portion of the mouth using the positioning arrangement; and fixating the positioning arrangement by means of an adhesive when said bite-block has been placed in position, thereby fixating the positioning arrangement.

Thus, the present invention is based on the idea of using at least two joints to freely positioning of a bite-block in a co-operating position with the upper palate of a mouth of a patient and thereafter fixating the bite-block in relation to the interface unit using an adhesive thereby enabling a quick fixation of the fixation device in a desired position, which, in turn, provides for an accurate and repeatable immobilisation of a head of a patient during treatment thereof. In addition, a tensionless fixation is easily achieved as well as comfortable treatment position of the patient, which provides for a high repositioning accuracy. Moreover, the positioning by means of joints entails that less material is situated in-front of the face of a patient during the treatment which ensures less artefacts in the radiation therapy result.

It should be noted that the term "immobilizing" as used herein is intended to refer to an element, i.e. the head of the patient, that is fixated by means of mechanical means, i.e. the fixation device, to reduce or eliminate motion thereof. In other words, the immobilized head maintains its position relative to the therapy unit via interface unit or the like.

Moreover, it should also be noted that the term "treatment" as used herein, e.g. "treatment unit", "treatment system" or "treatment of the head", is intended to refer to any kind of diagnosis, therapy or surgery inside the head of the patient, e.g. MRI, Biopsy, neurological diagnosis, therapy or surgery, or various radiation therapy treatment or the like. Thus, a treatment unit may for example be a radiation therapy unit, proton therapy unit, ultrasound therapy or the like. The embodiments of the invention are suitable for a fractionated treatment, e.g. a fractionated radiation therapy.

Also, the term "medical device" as used herein is intended to refer to any kind of devices used for diagnosis, therapy or surgery inside the head of the patient, e.g. a biopsy needle or the like.

It should also be noted that the term "frame" as used herein is intended to refer to an element for supporting another element, e.g. for supporting a medical device. In such a case, the frame, for instance a stereotactic frame, provides a support for the medical device that is used for performing said treatment.

Also, it should be noted that the term "interface unit" as used herein is intended to refer to an element by which a thereto connected bite-block via a positioning arrangement interacts with the treatment system. For example an interface unit may for example be a frame, i.e. element or structure made for supporting something. This interface unit is co-operatively connected to a second oppositely arranged interface unit of the treatment unit of the treatment system. Such second interface unit of the treatment unit may be a portion of the treatment system, e.g. a framework of a radiation therapy system or an auxiliary element thereto and is fixed relative to the treatment unit, e.g. a radiation unit.

In one embodiment of the present invention, the positioning arrangement connects the bite-block to the interface unit by means of at least two joints. The bite-block can thereby be freely positioned and re-positioned relative to the adaptor unit or frame and thereafter fixated such that a tensionless fixation is achieved.

According to an embodiment of the present invention, the interface unit is adapted to be removably connected to an adaptor unit or a frame. Alternatively, the adaptor unit is adapted to be removably connected to said treatment unit. The immobilization or fixation, which are individual for each patient, can be preserved by means of the removable interface unit thereby ensuring that the patient can be docked to the radiation therapy unit in a repeatable way to guarantee that the patient is positioned and repositioned in exact alignment to a reference position at every single treatment session.

According to an embodiment of the present invention, the positioning arrangement comprises an elongated linking arm having two opposite ends which are movably connected to the bite-block at a first end by means of a first joint respectively to the interface unit at a second end by means of a second joints. Thus, said arm is arranged with two oppositely arranged ends, wherein a first end connects the bite-block by means of a first joint. A second end connects the interface unit by means of a second joint. Thereby, enhancing a flexible and tensionless fixation of the bite-block relative to the adaptor unit or frame.

In one embodiment of the present invention, the linking arm is a telescopic arm, wherein the bite-block can be extracted or retracted relative the interface unit. Thus, the linking arm is adjusted in a telescopic manner, i.e. in a elongation and compression manner, to adjust the length of the linking arm. This contributes to a tensionless and flexible fixation even further.

In one embodiment of the present invention, the linking arm comprises a first and second linking arm portion being movably connected to each other by means of a third joint also adapted to be fixated by means of an adhesive. This enables a variable and freely positioning and re-positioning of the bite-block, increasing even further to a tensionless fixation.

According to an embodiment of the present invention, the first and/or the second linking arm portion is a telescopic arm portion, wherein the bite-block relative the interface unit can be extracted or retracted. This will increase the flexibility of the fixation even further.

In a further embodiment of the present invention, the at least two joints are ball-and-socket joints. A ball-and-socket joint or ball joint is a joint where a ball-shaped element moves within a co-operating socket, so as to allow rotary motion in every direction within certain limits. Such a joint enables a controlled positioning and re-positioning of the bite-block, which contributes to a tensionless fixation.

According to another embodiment of the present invention, the linking arm comprises an internal adhesive channel network adapted to supply the at least two joints with adhesive. This will ensure that the joints are quickly supplied with adhesive, which thereby increases the accuracy and stability of the fixation.

According to another embodiment of the present invention, the adhesive is an UV-curable adhesive. This will enable an easy fixation of the bite-block, since the bite-block can be positioned until a completely desirable position is achieved, then this position is locked by means of ultraviolet or UV radiation which thereby increases the accuracy and stability of the fixation.

According to another embodiment of the present invention, the step of providing a positioning arrangement adapted to movably connect the bite-block to the interface unit comprises the step of: providing at least two joints adapted to movably connect the bite-block to the interface unit. This will ensure a free positioning of the bite-block relative to the interface unit.

In an embodiment of the present invention, the step of providing the at least two joints comprises the steps of: providing the adhesive at the at least two joints; and curing the adhesive by means of ultraviolet radiation. Thereby, the bite-block may be positioned and repositioned as much as needed and when a satisfied position is achieved, then the adhesive is cured which will lock the bite-block in position. This will lead to an accurate locking of the positioned bite-block to the interface unit, which, in turn, ensures a tensionless fixation.

Moreover, according to another embodiment of the method of the invention, the method further comprises a step of releasing the patient from the bite-block and the interface unit from the adaptor unit or frame. Thereafter, the step of releasing the patient from the bite-block and interface unit from the adaptor unit or frame further comprises the steps of: re-fixating the patient relatively the interface unit by means of inserting the bite-block and thereafter re-fixating the interface unit relative to the adaptor unit or frame.

The adjustment of the head fixation, which is individual for each patient, can thereby be preserved. Thus, the patient can be docked to the treatment unit, e.g. radiation therapy unit in a repeatable way to guarantee that the patient is positioned and repositioned in exact alignment to a reference position at every single treatment session.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

Preferred embodiments of the invention will now be described in greater detail with reference to the accompanying drawings, in which.

DESCRIPTION OF PREFERRED EMBODIMENTS

First, with reference to FIGS. 1-3, a radiation therapy system for which the present invention is applicable comprises a radiation therapy unit or radiation unit 10 and a patient positioning unit 20 will be described. In the radiation unit 10, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels. Examples of collimator arrangements in radiation therapy systems applicable to the present invention can be found in U.S. Pat. No. 6,931,096, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the present inventions is also applicable to LINAC radiosurgical systems, in which a collimated x-ray beam is focused on a stereotactically identified intracranial target and the gantry of the LINAC rotates around the patient, producing an arc of radiation focused on the target.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit, either directly or via an adaptor unit 42, see FIG. 3. A head can according to the present invention, for example, a rigid casing enclosing the head of the patient (which will be described in more detail below with reference to FIGS. 4 and 5) is attachable to the patient fixation frame, see FIG. 3.

The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

The fixation arrangement 28 comprises two engagement points 30, 32, which are arranged for preventing the patient fixation unit from translational and/or rotational movement in relation to the movable carriage 24.

Figure 1:
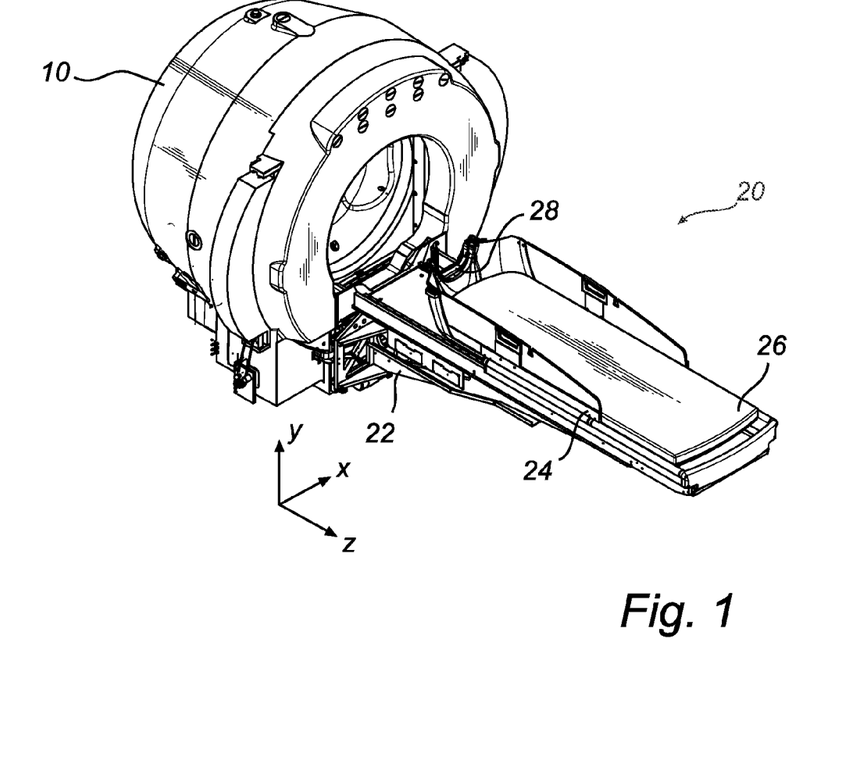
FIG. 1 illustrates the general principle of a radiation therapy system in which the present invention may be used.
Figure 2:
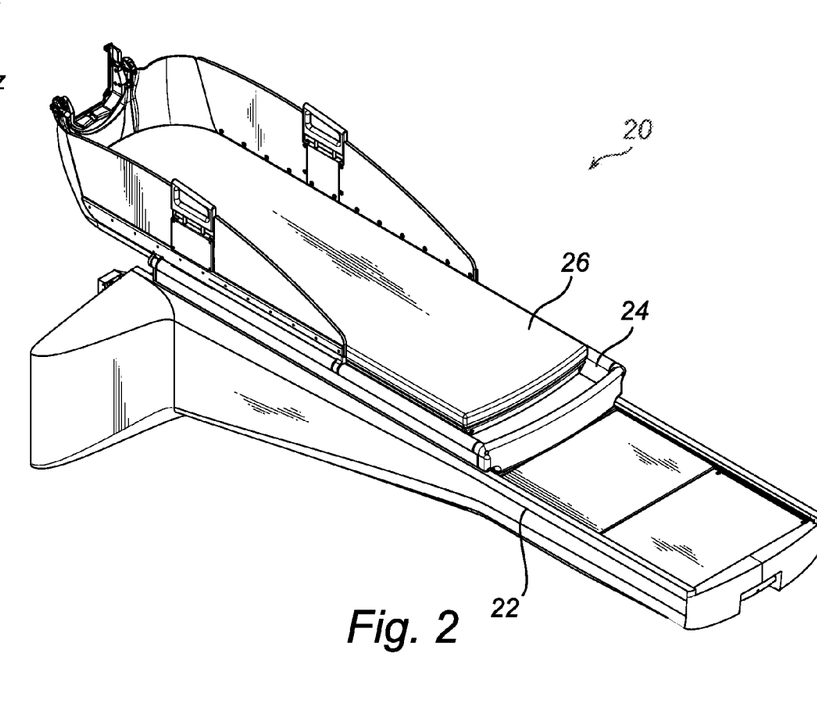
FIG. 2 illustrates the positioning unit used in the system of FIG. 1.
Figure 3:
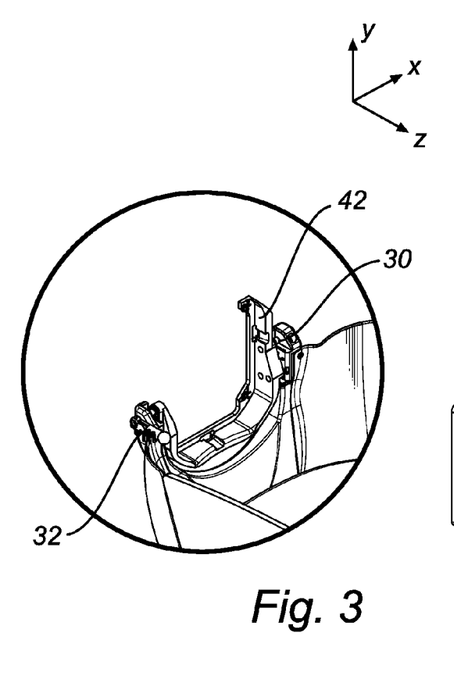
FIG. 3 illustrates a part of the positioning unit including the engagement points for holding a fixation interface unit in more detail.

As can be understood from FIGS. 1 and 2, the described embodiment concerns a radiation therapy system for providing gamma radiation therapy to a target volume in the head of human patient. Such therapy is often referred to as stereotactic radiation surgery. During therapy, the patient head is fixed in a fixation unit in the form of a stereotactic head frame, which comprises engagement points adapted for engagement with the engagement points 30, 32 of the radiation therapy system. Thus, during the stereotactic radiation surgery, the head of the patient is fixed in the stereotactic frame, which in turn is fixedly attached to the patient positioning unit via the engagement points 30, 32. During movement of the treatment volume in the head of the patient in relation to the radiation focus point, along the three orthogonal axes x, y, and z shown in FIG. 1, the entire patient is moved along the axes. Thus, there is no relative movement between the head frame and the carriage 24 of the patient positioning unit 20.

Figure 4:
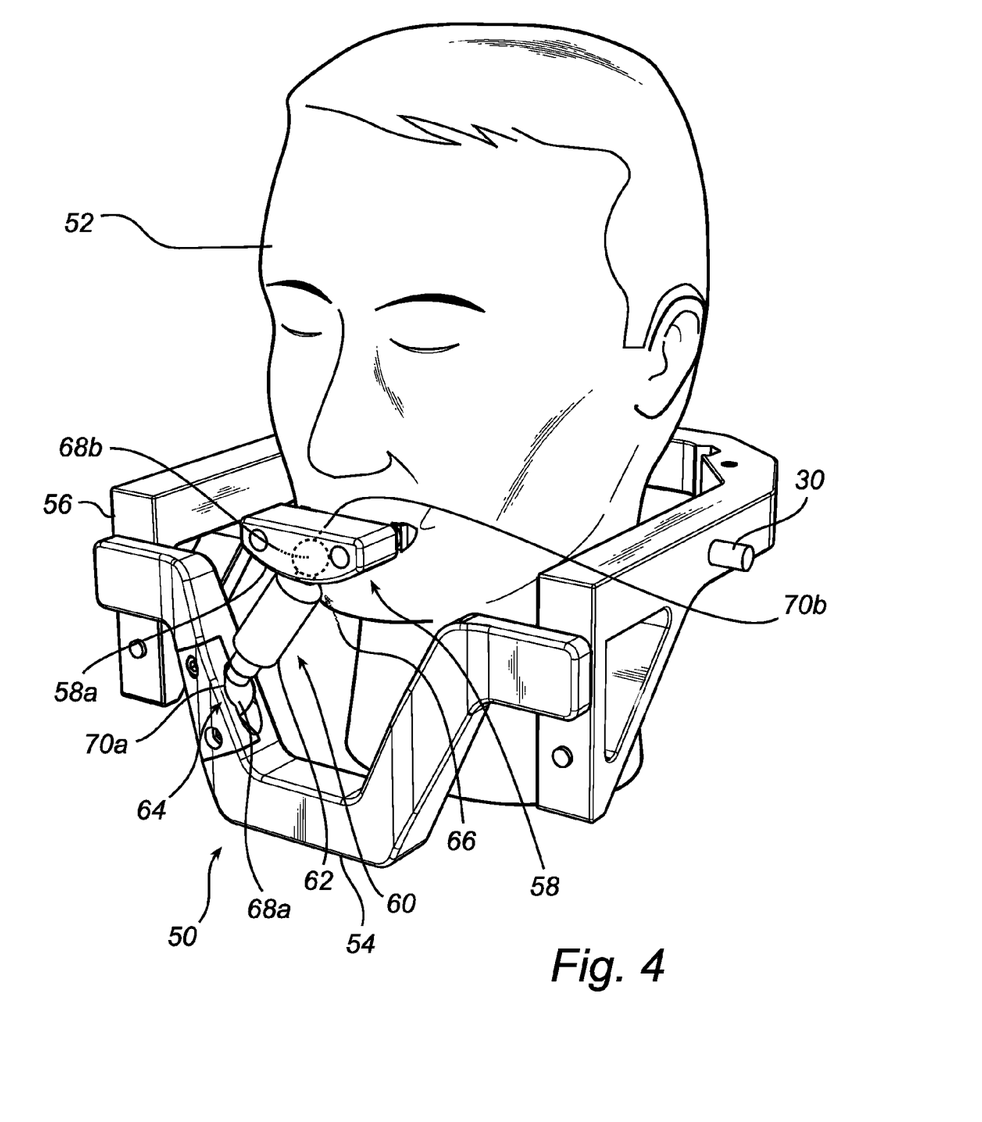
FIG. 4 illustrates a fixation device according to an embodiment of the present invention.

With reference to FIG. 4, an embodiment of the fixation device according to the invention is shown. The fixation device 50 for immobilizing a head 52 of a patient relative a radiation therapy unit or other treatment unit during neurological diagnosis, therapy or surgery or another treatment, is now discussed. An interface unit 54 of the fixation device 50 is connected to an adapter unit 56, which via engagement points 30 and 32 (not shown) is connected to the patient positioning unit 20 of the radiation therapy system. Thus, the adapter unit is a part of the patient positioning unit 20. As is understood, the interface unit 54 may also, without any adaptor unit, be directly connected to the positioning unit 20. A bite-block 58 is inserted into a mouth of the head 52 of a patient. Furthermore, a surface (not shown), or at least a portion, of the bite-block 58 co-operates with the upper palate of the mouth. The bite-block 58, i.e. an external portion 58a of the bite-block that protrudes from the mouth when the block 58 is inserted into the mouth, is connected to the interface unit 54 by means of a positioning arrangement 60. The positioning arrangement 60 of FIG. 4 comprises an elongated linking arm 62, which is connected at its two distal ends to the bite-block and the interface unit, respectively, by means of two joints 64 and 66.

Part from being an adaptor arrangement between the interface unit 54 and the fixation arrangement of a radiation treatment system, it is to be understood that the adaptor unit 56 herein described and shown may also be a frame for supporting medical devices, such as a biopsy needle device or the like.

As mentioned above, the bite-block 58 is adapted to co-operate with the upper palate of the mouth when inserted. However, the bite-block may co-operate with another portion of the mouth, other than the upper palate. Preferably, such a portion is connected to the skull or cranium, such that a fixation of the bite-block results in a fixation of the skull or cranium, or more specifically, the intracranial target.

In order to enable a correct repositioning of the head in a fractionated session, these two joints 64 and 66 can be fixated by means of an adhesive (not shown) to fixate the bite-block, which is in a co-operation position with the upper palate of the mouth of the patient, in relation to the interface unit such that the head 52 of the patient can be immobilized relative a radiation therapy unit (not shown). In the fixation method, the adhesive may be an UV-curable adhesive which is an adhesive that is cured by means of ultraviolet radiation or other curable radiation. Consequently, the bite-block can be repeatedly adjusted or repositioned until a satisfied or ideal position is achieved, whereby the curing step is performed.

Alternatively, other adhesive, such as drying, contact and hot adhesives, may be applied to the joints, for example in between a pair of co-operating surfaces forming the joint. Then this adhesive hardens, thereby locking the position of respective surface to each other and, thus, locking the bite-block in relation to the interface unit.

Figure 5:
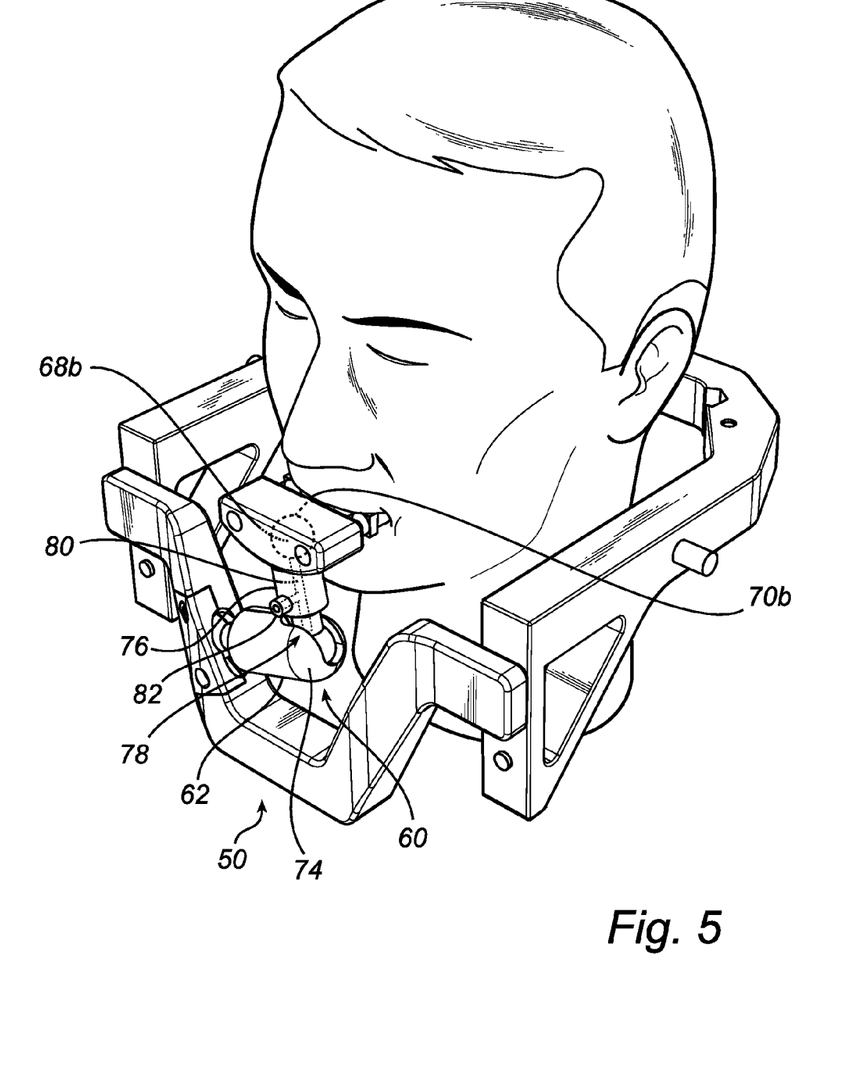
FIG. 5 illustrates a fixation device according to another embodiment of the invention.

In the embodiments of FIGS. 4 and 5 the first and second joints 64 and 66 are of ball-and-socket type. Such a ball-and-socket joint 64 and 66 is a joint in which a ball 68a and 68b moves within a socket 70a and 70b, respectively, so as to allow rotary motion in every direction within certain limits. Thus, the bite-block 58 is movably connected to interface unit 54 by means of the two joints 64 and 66 which enables a very flexible fitting to the patient. Although both distal ends of the elongated linking arm 62 in FIGS. 4 and 5 are provided with balls 68a and 68b, the ball-and-socket joints may be reversely arranged such that the distal ends are formed as sockets and that the balls are arranged at the interface unit and bite-block, respectively.

The linking arm 62 in FIG. 4 is rigid in the direction between the balls. However, the linking arm may also be a telescopic arm for adjusting the length of the arm, i.e. the distance between the ball provided ends. Thus, the arm 62 can be extracted or retracted relative the interface unit, i.e. adjusting the protruding distance of the bite-block relative the interface unit.

In FIGS. 4 and 5, the interface unit 54 of the fixation device 50 according to the invention is removably connected to an adaptor unit by means of a snap locking arrangement. However, other alternative arrangement may also be used, such as a screw means. As discussed above, the interface unit 54 may also be directly connected to the positioning unit 20 by means of the snap locking arrangement, without any adaptor unit 56. Although FIGS. 4 and 5 only shows a two positional snap locking arrangement in which the interface unit 54 may snap lock the adaptor unit 56, it is understood that interface unit may be connected to the adaptor unit, or directly to the positioning unit 20, at further positions. Furthermore, the snap locking arrangement may also be a continuously variable locking arrangement, or a combination of these two arrangement. For example, a snap locking arrangement could be positioned and locked at a preferred position by means of the continuously variable locking arrangement. In such a case, only a one-positional snap locking arrangement is required. However, this implies that position of the variable locking arrangement relative the adaptor and/or interface unit can be preserved for an accurate repositioning of the head.

Referring to FIG. 5, a fixation device 50 according to another embodiment of the invention is shown. The linking arm 62 of the positioning arrangement 60 is here provided with a first and second linking arm portion 74 and 76, which are connected to each other by means of a third joint 78. This third joint is also a joint of a ball-and-socket type. As discussed above the third joint may also be reversed, i.e. the ball and socket switch places. Furthermore, in the same manner as above the third joint 78 is also fixated by means of an adhesive. The first and/or the second linking arm portion 74 and 76 may also be a telescopic arm portion. Moreover, the second linking portion 76 is provided with an internal adhesive channel 80, which is adapted to supply the second joint 70b with an adhesive (not shown). An inlet 82 is in connection with the adhesive channel 80. The internal adhesive channel 80 may be a part of an internal adhesive channel network (not shown) to supply adhesive to respective joint.

As is understood the fixation device 50 according to the invention may also be provided with further linking arm portions.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A fixation device for immobilizing a head of a patient relative a treatment unit or medical device during treatment of the head, the fixation device comprising
   an interface unit adapted to be fixated in relation to an adaptor unit for connection to the treatment unit, or to a frame for connection to the medical device;

a bite-block for being inserted into a mouth of a patient; and a positioning arrangement movably connecting the bite-block to the interface unit, wherein the positioning arrangement is adapted to be fixated by means of an adhesive for fixation of the bite-block such that the head of a patient can be immobilized relative to said adaptor unit or frame wherein the positioning arrangement comprises an elongated linking arm having two opposite ends which are movably connected to the bite-block at a first end by means of a first joint respectively to the interface unit at a second end by means of a second joint, and wherein the linking arm comprises an internal adhesive channel network adapted to supply the two joints with adhesive.

2. The fixation device according to claim 1, wherein the positioning arrangement connects the bite-block to the interface unit by means of at least two joints.

3. The fixation device according to claim 2, wherein the at least two joints are ball-and-socket joints.

4. The fixation device according to claim 1, wherein the interface unit is adapted to be removably connected to an adaptor unit or a frame.

5. The fixation device according to claim 4, wherein the adaptor unit is adapted to be removably connected to said treatment unit.

6. The fixation device according to claim 1, wherein the linking arm comprises a first and second linking arm portion being movably connected to each other by means of a third joint also adapted to be fixated by means of an adhesive.

7. The fixation device according to claim 6, wherein the first linking arm portion is a telescopic arm portion, wherein the bite-block relative the interface unit can be extracted or retracted.

8. The fixation device according to claim 1, wherein the linking arm is a telescopic arm, wherein the bite-block can be extracted or retracted relative the interface unit.

9. The fixation device according to claim 1, wherein the adhesive is an UV-curable adhesive.

10. The fixation device according to claim 1, wherein the first joint and the second joint are ball-and-socket joints.

11. A method for immobilizing a head of a patient relative a treatment unit or a medical device during treatment of the head, said method comprising the steps of:

providing an interface unit adapted to be fixated in relation to an adaptor unit for connection to the treatment unit, or to a frame for connection to the medical device;

providing a bite-block adapted to be inserted into a mouth of a patient;

providing a positioning arrangement adapted to movably connect the bite-block to the interface unit, the positioning arrangement comprising an elongated linking arm having two opposite ends which are movably connected to the bite-block at a first end by means of a first joint respectively to the interface unit at a second end by means of a second joint, wherein the linking arm comprises an internal adhesive channel network;

positioning the bite-block in a co-operating position with a portion of the mouth using the positioning arrangement; and fixating the positioning arrangement by means of an adhesive when said bite-block has been placed in position, thereby fixating the positioning arrangement such that the head of the patient is immobilized relative to said adaptor unit or frame, said fixating supplying said joints with adhesive via said internal adhesive channel network.

12. The method according to claim 11, wherein the step of providing a positioning arrangement adapted to movably connect the bite-block to the interface unit comprises the step of: providing at least two joints adapted to movably connect the bite-block to the interface unit.

13. The method according to claim 12, wherein the step of providing the at least two joints comprises the steps of: providing the adhesive at the at least two joints; and curing the adhesive by means of ultraviolet radiation.

14. The method according to claim 11, wherein the method further comprises a step of releasing the patient from the bite-block and the interface unit from the adaptor unit or frame.

15. The method according to claim 14, wherein the step of releasing the patient from the bite-block and interface unit from the adaptor unit or frame further comprises the steps of: re-fixating the patient relative to the interface unit by means of inserting the bite-block and thereafter re-fixating the interface unit relative to the adaptor unit or frame.

* * * * *

UNITED STATES PATENT AND TRADEMARK OFFICE
CERTIFICATE OF CORRECTION

| | | |
|---|---|---|
| PATENT NO. | : 8,567,405 B2 | Page 1 of 1 |
| APPLICATION NO. | : 12/988885 | |
| DATED | : October 29, 2013 | |
| INVENTOR(S) | : Thomas Arn et al. | |

It is certified that error appears in the above-identified patent and that said Letters Patent is hereby corrected as shown below:

ON THE TITLE PAGE:

Item (75), Inventors, change "Kristian Wiberg, Ävsjö (SE)" to --Kristian Wiberg, Älvsjö (SE)--.

Signed and Sealed this
Eighteenth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,567,405 B2  Page 1 of 1
APPLICATION NO. : 12/988885
DATED : October 29, 2013
INVENTOR(S) : Arn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

Signed and Sealed this
Fifteenth Day of September, 2015

Michelle K. Lee
*Director of the United States Patent and Trademark Office*